US006482831B1

(12) United States Patent
Wynn et al.

(10) Patent No.: US 6,482,831 B1
(45) Date of Patent: Nov. 19, 2002

(54) COVALENTLY COUPLED BENZOYLECGONINE, EGCONINE AND ECGONIDINE DERIVATIVES

(75) Inventors: James E. Wynn, Summerville, SC (US); Lowell M. Somers, Indio, CA (US)

(73) Assignee: Entropin, Inc., Indio, CA (US)

( * ) Notice: Subject to any disclaimer, the term of this patent is extended or adjusted under 35 U.S.C. 154(b) by 0 days.

(21) Appl. No.: 09/558,534

(22) Filed: Apr. 26, 2000

Related U.S. Application Data

(60) Division of application No. 09/063,820, filed on Apr. 21, 1998, which is a division of application No. 08/750,901, filed as application No. PCT/US95/09726 on Jun. 14, 1995, which is a continuation-in-part of application No. 08/260,054, filed on Jun. 16, 1994, now Pat. No. 5,525,613.

(51) Int. Cl.[7] .................... A61K 31/439; C07D 451/02; C07D 451/04

(52) U.S. Cl. ........................ 514/301; 546/128; 546/130

(58) Field of Search .......................... 514/304; 546/128, 546/130

(56) References Cited

U.S. PATENT DOCUMENTS

| | | | |
|---|---|---|---|
| 2,893,996 A | 7/1959 | Rudner et al. | 260/292 |
| 2,948,730 A | 8/1960 | Rudner et al. | 260/292 |
| 4,469,700 A | 9/1984 | Somers | 424/265 |
| 4,512,996 A | 4/1985 | Somers | 514/304 |
| 4,556,663 A | 12/1985 | Somers | 514/304 |
| 5,376,667 A | 12/1994 | Somers et al. | 514/304 |
| 5,525,613 A | 6/1996 | Wynn et al. | 514/304 |
| 5,559,123 A | 9/1996 | Somers et al. | 514/304 |
| 5,763,456 A | 6/1998 | Wynn et al. | 514/304 |
| 6,077,848 A | 6/2000 | Wynn et al. | 514/304 |

FOREIGN PATENT DOCUMENTS

| | | | | |
|---|---|---|---|---|
| FR | 2569563 A1 | 3/1986 | .......... | A61K/31/46 |
| WO | WO 94 15935 | 7/1994 | .......... | C07D/451/12 |

OTHER PUBLICATIONS

W.H. Anderson and D.T. Stafford, "Applications of Capillary Gas Chromatography in Routine Toxicological Analyses", *J. High Resolut. Chromatogr., Chromatogr. Commun.*, 6, pp. 247–254 (1983).
E.J. Ariens and A.M. Simonis, "A Molecular basis for drug action. The interaction of one or more drugs with different receptors", *J. Pharm. Pharmacol.*, 16, pp. 289–312 (1964).
M.R. Bell and S. Archer, "L(+)–2–Tropinone", *J. Amer. Chem. Soc.*, 82, pp. 4642–4644 (1960).
R. Bingham, "Esterene in the Treatment of Rheumatoid Arthritis", *Arthritis News Today*, 2(7), pp. 1–4 (1980).

C.S. Boyer and D.R. Peterson, "Enzymatic Basis for the Transesterification of Cocaine in the Presence of Ethanol: Evidence for the Participation of Microsomal Carboxylesterases", *J. Pharmacol. Exp. Ther.*, 260(3), pp. 939–946 (1992).
M.R. Brzezinski et al., "Convenient Synthesis of Benzoylecgonine Ethyl Ester, a Homolg of Cocaine", *Synth. Commun.*, 22(7), pp. 1027–1032 (1992).
R.D. Budd, "Cocaine Radioimmunoassay—Structure Versus Reactivity", *Clin. Toxicol.*, 18(7), pp. 773–782 (1981).
D.T. Chia and J.A. Gere, "Rapid Drug Screening Using Toxi–Lab® Extraction Followed by Capillary Gas Chromatography/Mass Spectroscopy", *Clin. Biochem.*, 20(5), pp. 303–306 (1987).
A.J. Clark, "The Antagonism of AceTyl Choline by Atropine", *J. Physiol.*, 61, pp. 547–556 (1926).
E.J. Cone et al., "Testing Human Hair for Drug Abuse. II. Identification of Unique Cocaine Metabolites in Hair of Drug Abusers and Evaluation of Decontamination Procedures", *J. Anal. Toxicol.*, 15(5), pp. 250–255 (1991).
R.A. Dean et al., "Human Liver Cocaines Esterases: Ethanol–Mediated Formation of Ethylcocaine", *FASEB J.*, 5(12), pp. 2735–2739 (1991).
F. Fish and W.D.C. Wilson, "Excretion of Cocaine and its Metabolites in Man", *J. Pharm. Pharmac.*, 21 suppl., pp. 135S–138S (1969).
J.R. Fozard et al., "Structure–Activity Relationship of Compounds Which Block Receptors for 5–Hydroxytryptamine on the Sympathetic Nerves of the Rabbit Heart", *Br. J. Pharmacol.*, 61(3), pp. 499P–500P (1977).
J.R. Fozard et al., "Blockade of Serotonin Receptors on Autonomic Neurones by (−)–Cocaine and Some Related Compounds", *Eur. J. Pharmacol.*, 59(3–4), pp. 195–210 (1979).
J.H. Gaddum, "The Action of Adrenalin and Ergotamine on the Uterus of the Rabbit", *J. Physiol.*, 61, pp. 141–150 (1926).
J.H. Gaddum, "The Quantitative Effects of Antagonistic Drugs", *J. Physiol.*, 89, pp. 7–9 (1937).
C. Hansch and W.J. Dunn, "Linear Relationships between Lipophilic Character and Biological Activity of Drugs", *J. Pharm. Sci.*, 61, pp. 1–19 (1972).
W.L. Hearn et al., "Cocaethylene is More Potent than Cocaine in Mediating Lethality", *Pharmacol., Biochem. Behav.*, 39(2), pp. 531–533 (1991).

(List continued on next page.)

Primary Examiner—Alan L. Rotman
Assistant Examiner—Janet L. Coppins
(74) Attorney, Agent, or Firm—Fish & Neave; Denise L. Loring; Nina R. Horan

(57) ABSTRACT

The present invention relates to a novel class of covalently coupled benzoylecgonine, ecgonine and ecgonidine derivatives that are useful for alleviating the symptoms of immunoregulatory disorders, neuromuscular disorders, joint disorders, connective tissue disorders, circulatory disorders and pain. Accordingly, this invention also relates to pharmaceutical compositions and methods for their use.

10 Claims, No Drawings

OTHER PUBLICATIONS

W.L. Hearn et al., "Cocaethylene: A Unique Cocaine Metabolite Displays High Affinity for the Dopamine Transporter", *J. Neurochem.,* 56(2), pp. 698–701 (1991).

G.W. Hime et al., "Analysis of Cocaine and Coaethylene in Blood and Tissues by GC–NPD and GC–Ion Trap Mass Spectrometry", *J. Anal. Toxicol.,* 15(5), pp. 241–245 (1991).

P. Jatlow et al., "Cocaethylene: A Neuropharmacologically Active Metabolite Associated with Concurrent Cocaine–Ethanol Ingestion", *Life Sci.,* 48(18), pp. 1787–1794 (1991).

J.L. Katz et al., "Comparative Behavioral Pharmacology and Toxicology of Cocaine and its Ethanol–Derived Metabolite, Cocaine Ethyl–Ester (Cocaethylene)", *Life Sci.,* 50(18), pp. 1351–1361 (1992).

A. Leo et al., "Partition Coefficients and Their Uses", *Chemical Reviews,* 71, pp. 525–616 (1971).

A.H. Lewin et al., "2β–Substituted Analogues of Cocaine. Synthesis and Inhibition of Binding to the Cocaine Receptor", *J. Med. Chem.,* 35(1), pp. 135–140 (1992).

T. Lukaszewski and W.K. Jeffery, "Impurities and Artifacts of Illicit Cocaine", *J. Forensic Sci.,* 25(3), pp. 499–507 (1980).

H.H. McCurdy, "Quantitation of Cocaine and Benzoylecgonine after JETUBE® Extraction and Derivitazation", *J. Anal. Toxicol.,* 4(2), pp. 82–85 (1980).

*Medical World News,* "FP Giving Cocaine for Arthritis is Beset But Gains a Major Ally", pp. 19–20 (1979).

A.L. Misra et al., "Physiologic Disposition and Metabolism of [$^3$H]–Ecgonine (Cocaine Metabolite) in the Rat", *Res. Commun. Chem. Pathol. Pharmacol.,* 8, pp. 55–63 (1974).

A.L. Misra and S.J. Mule, "Calcium–Binding Property of Cocaine and Some of its Active Metabolites—Formation of Molecular Complexes", *Res. Comm. Chem. Pathol. Pharmacol.,* 11(4), pp. 663–666 (1975).

A.L. Misra et al., "Disposition of [$^3$H]–Benzoylnorecgonine (Cocaine Metabolite) in the Rat", *Res. Commun. Chem. Pathol. Pharmacol.,* 13(4), p. 579–83 (1976).

A.L. Misra et al., "Estimation and Disposition of [$^3$H]–Benzoylecgonine and Pharmacological Activity of Some Cocaine Metabolites", *J. Pharm. Pharmac.,* 27, pp. 784–786 (1975).

C. Moore et al., "Determination of Cocaine and its Metabolites in Brain Tissue Using High–Flow Solid–Phase Extraction Columns and High–Performance Liquid Chromatography", *Forensic Sci. Int.,* 53(2), pp. 215–219 (1992).

S.J. Mule et al., "Intracellular Disposition of [$^3$H]–Cocaine, [$^3$H]–Norcocaine, [$^3$H]–Benzoylecgonine and [$^3$H]–Benzoylnorecgonine in the Brain of Rats", *Life Sci.,* 19, pp. 1585–1596 (1976).

M. Perez–Reyes and A.R. Jeffcoat, "Ethanol/Cocaine Interaction: Cocaine and Cocaethylene Plasma Concentrations and Their Relationship to Subjective and Cardiovascular Effects", *Life Sci.,* 51(8), pp. 553–563 (1992).

M. Polášek et al., "Determination of Limiting Ionic Mobilities and Dissociation Constants of Some Local Anaesthetics", *J. Chromatogr.,* 596, pp. 265–270 (1992).

F.K. Rafla and R.L. Epstein, "Identification of Cocaine and its Metabolites in Human Urine in the Presence of Ethyl Alcohol", *J. Anal. Toxicol.,* 3(2), pp. 59–63 (1979).

M.E.A. Reith et al., "Locomotor Effects of Cocaine, Cocaine Congeners and Local Anesthetics in Mice", *Pharmacol. Biochem. Behav.,* 23(5), pp. 831–836 (1985).

M.E.A. Reith et al., "Structural Requirements for Cocaine Congeners to Interact with [$^3$H] Batrachotoxinin a 20–α–Benzoate Binding Sites on Sodium Channels in Mouse Brain Synaptosomes", *J. Biol. Chem.,* 261(16), pp. 7300–7305 (1986).

M.E.A. Reith et al., "Structural Requirements for Cocaine Congeners to Interact with Dopamine and Serotonin Uptake Sites in Mouse Brain and to Induce Stereotyped Behavior", *Biochem. Pharmcol.,* 35(7), pp. 1123–1129 (1986).

S.M. Roberts et al., "Cocaethylene Hepatoxicity in Mice", *Biochem. Pharmacol.,* 43(9), pp. 1989–1995 (1992).

S.M. Roberts et al., "An Assay for Cocaethylene and Other Cocaine Metabolites in Liver Using High–Performance Liquid Chromatography", *Anal. Biochem.,* 202(2), pp. 256–261 (1992).

R.H. Rohrbaugh and P.C. Jurs, "Prediction of Gas Chromatographic Retention Indexes for Diverse Drug Compounds", *Anal. Chem.,* 60(20), pp. 2249–2253 (1988).

H.–L. Schmidt and G. Werner, "Synthetischer Einbau von $^{14}$C in (–)–Cocain,(–)–Ekgonin und Derivate", *Ann.,* pp. 184–194 (1961).

R.M. Smith, "Ethyl Esters of Arylhydroxy–and Arylhydroxymethoxycocaines in the Urines of Simultaneous Cocaine and Ethanol Users", *J. Anal. Toxicol.,* 8(1), pp. 38–42 (1984).

R.P. Stephenson, "A Modification of Receptor Theory", *Brit. J. Pharmacol.,* 11, pp. 379–393 (1956).

D.L. Von Minden and N.A. D'Amato, "Simultaneous Determination of Cocaine and Benzoylecgonine in Urine by Gas–liquid Chromatography", *Anal. Chem.,* 49(13), pp. 1974–1977 (1977).

G. Werner and K.H. Störr, "Labelled Tropane Alkaloids. VI. Synthesis of [N–methyl–T1] Psicain–nue and of Polytopically Tritiated Psicain", *Liebigs Ann. Chem.,* pp. 1650–1654 (1974).

J.J. Woodward et al., "Cocaethylene Inhibits Dopamine Uptake and Produces Cocaine–Like Actions in Drug Discrimination Studies", *Eur. J. Oharmacol.,* 197(2–3), pp. 235–236 (1991).

I. I. Zimaányi et al., "Effect of Cocaine and Cocaine Congeners on Veratridine–Induced Depolarization in Mouse Cerebrocortical Synaptoneurosomes", *J. Neurosci. Res.,* 22(2), pp. 201–208 (1989).

COVALENTLY COUPLED BENZOYLECGONINE, EGCONINE AND ECGONIDINE DERIVATIVES

TECHNICAL FIELD OF THE INVENTION

The present invention relates to a novel class of covalently coupled benzoylecgonine, ecgonine and ecgonidine derivatives that are useful for alleviating the symptoms of immunoregulatory disorders, neuromuscular disorders, joint disorders, connective tissue disorders,. circulatory disorders and pain. Accordingly, this invention also relates to pharmaceutical compositions and methods for their use.

BACKGROUND OF THE INVENTION

Benzoylecgonine, ecgonine and ecgonidine are known metabolites of cocaine (see, for example, S. M. Roberts et al., "An Assay for Cocaethylene and Other Cocaine Metabolites in Liver Using High-Performance Liquid Chromatography", *Anal. Biochem.*, 202, pp. 256–61 (1992); D. T. Chia and J. A. Gere, "Rapid Drug Screening Using Toxi-Lab Extraction Followed by Capillary Gas Chromatography/Mass Spectroscopy", *Clin.Biochem.*, 20, pp. 303–06 (1987)). Routes for their preparation have been established (see, for example, A. H. Lewin et al., "2β-Substituted Analogues of Cocaine. Synthesis and Binding to the Cocaine Receptor", *J. Med. Chem.* 35, pp. 135–40 (1992); M. R. Bell and S. Archer, "L(+)-2-Tropinone", *J. Amer. Chem. Soc.* 82, pp. 4642–44 (1960)).

We have demonstrated the pharmaceutical efficacy of benzoylecgonine and ecgonine in the treatment of rheumatoid arthritis, osteoarthritis and related inflammatory disorders (see, for example, U.S. Pat. Nos. 4,469,700, 4,512,996 and 4,556,663). We have also demonstrated the pharmaceutical efficacy of certain 2-β-derivatized analogues of benzoylecgonine, ecgonine and ecgonidine (see, for example, co-pending U.S. Pat. application Ser. No. 07/999, 307). We have now discovered a new class of easily synthesized, covalently coupled benzoylecgonine, ecgonine and ecgonidine derivatives that have novel therapeutic features and improve certain therapeutic properties of underivatized benzoylecgonine, ecgonine and ecgonidine.

SUMMARY OF THE INVENTION

It is a principal object of this invention to provide easily synthesized, covalently linked benzoylecgonine, ecgonine and ecgonidine derivatives which are useful for alleviating the symptoms of immunoregulatory disorders, neuromuscular disorders, joint disorders, connective tissue disorders, circulatory disorders and pain.

The benzoylecgonine, ecgonine and ecgonidine derivatives of this invention are represented by formulas I and II, respectively:

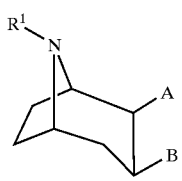
(I)

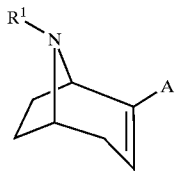
(II)

wherein:

each $R^1$ is independently selected from the group consisting of H; $COR^2$; COBn; alkyl; alkenyl; and alkynyl, said alkyl, alkenyl and alynyl being optionally substituted with OH, SH, $NH_2$, CN, $CF_3$ or halogen;

A is —L—(Kp;

B is —L—(M')$_{p'}$;

each p and p' is independently selected from the group consisting of 1 or 2;

each L is independently a linker which,
(a) if linking one M or M' to the ring system, is selected from the group consisting of —$(CR^2R^2)_n$—CO—Q—; —$(CR^2R^2)_n$—Q—CO—; —$(CR^2R^2)_n$—O—C(OH)—; and —$(CR^2R^2)_n$—Q—; or
(b) if linking two M or M', the same or different, to the ring system is

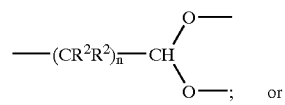   or (c) if linking two ring systems chosen from compounds of formulas I and II, the same or different, to M or M' is

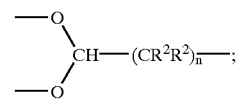

each n is independently selected from the group consisting of 0, 1, 2 and 3;

each Q is independently selected from the group consisting of —NH—, —O— and —S—;

each M and M' is independently a moiety that, either alone or in combination with other M or M' moieties, enhance the distribution characteristics, intrinsic activity or efficacy of said compound, provided that M is not a moiety having the formula —$CH_2$—CHX—$R^3$ when B is —O—CO—M', —O—M' or when B is not present (i.e., in compounds of formula II);

each $R^2$ is independently selected from the group consisting of H; alkyl; alkenyl; alkynyl; alkoxy; aminoalkyl; haloalkyl; aryl; heterocyclyl; aralkyl; cycloalkyl; cycloalkylalkyl; halogen; aroyl, acyl; and aralkyl; any of said $R^2$ being optionally substituted with OH, SH, $NH_2$, oxo and halogen;

X is selected from the group consisting of OH; SH; $NH_2$; and halogen; and $R^3$ is selected from the group consisting of alkyl, alkenyl and alkynyl, optionally substituted with OH, SH, $NH_2$ or halogen; $COCH_3$; COPh; and COBn.

It is a further object of this invention to provide pharmaceutical compositions comprising compounds of formulas I and II, and mixtures thereof.

It is also an object of this invention to provide methods for alleviating the symptoms of immunoregulatory disorders, neuromuscular disorders, joint disorders, connective tissue disorders, circulatory disorders and pain using the compounds and pharmaceutical compositions described herein.

DETAILED DESCRIPTION OF THE INVENTION

In accordance with this invention, the following definitions apply:

The following abbreviations are used herein:

Bn=benzyl radical; and Ph=phenyl radical.

The term "alkyl", alone or in combination, refers to a straight chain or branched chain alkyl radical having from one to ten, preferably from one to six, carbon atoms. Examples of such alkyl groups are methyl, ethyl, propyl, isopropyl, butyl, isobutyl, pentyl, neopentyl, hexyl and isohexyl.

The terms "alkenyl" and "alkynyl", alone or in combination, refer to a straight chain or branched chain alkenyl or alkynyl radical, respectively, having from two to ten, preferably from two to six, carbon atoms. The alkenyl radicals can be in the cis, ans, E— or Z— form. Examples of such alkenyl radicals are vinyl, ethenyl, propenyl and 1,4-butadienyl. Examples of alkynyl radicals are ethynyl and propynyl.

The term "alkoxy", alone or in combination, refers to an alkyl ether radical, wherein alkyl is defined as above. Examples of such alkoxy radicals are methoxy, ethoxy, n-propoxy, isopropoxy, n-butoxy and tert-butoxy.

The terms "aralkyl", "aminoalkyl" and "haloalkyl", alone or in combination, refer to an alkyl radical as defined above wherein one hydrogen atom is replaced by an aryl radical, an amino radical or a halogen radical, respectively. The aryl, amino or halogen radical may be located on the terminal carbon or an internal carbon of the alkyl radical.

The term "aryl", alone or in combination, refers to a phenyl or naphthyl radical optionally substituted with one or more substituents selected from the group consisting of alkyl, alkoxy, halogen, hydroxy, amino, nitro, cyano and haloalkyl. The aryl radical may be attached through any member of the ring that results in the creation of a stable structure. Examples of such aryl radicals include tolyl, xylyl, cymyl, mesityl and phenyl. The most preferred aryls are phenyl and phenyl substituted with alkyl having from one to five carbon atoms.

The term "aroyl" refers to an acyl radical derived from an aromatic carboxylic acid. Examples of such aroyl radicals include optionally substituted benzoic acid and naphthoic acid, such as benzoyl, 4-chlorobenzoyl, 4-carboxybenzoyl, 4-(benyloxycarbonyl)benzoyl, 1-naphthoyl, 2-naphthoyl, 6-carboxy-2-naphthoyl, 6-(benzyloxycarbonyl)-2-naphthoyl and 3-hydroxy-2-naphthoyl.

The terms "benzoylecgonine compound", "ecgonine compound" and "ecgonidine compound" refer not only to those compounds, but also to the corresponding 2-β derivatized analogs (such as the corresponding 2-β acids and 2-β alcohols) of benzoylecgonine, ecgonine, ecgonidine and the compounds of formulas I and II. For example, the 2-β acid of a compound of formula II will be referred to herein as an ecgonidine compound.

The term "acyl" refers to an alcyl radical as defined above linked via a carbonyl.

The term "cycloalkyl", alone or in combination, refers to a monocyclic, bicyclic or tricyclic alkyl radical, wherein each cyclic moiety contains from about three to about eight carbon atoms. Examples of such cycloalkyl radicals are cyclopropyl, cyclobutyl, cyclopentyl and cyclohexyl.

The term "cycloalkylalkyl" refers to an alkyl radical as defined above which is substituted with a cycloalkyl radical containing from about three to about eight carbon atoms.

The term "distribution characteristics" refers to the ability of a molecule to reach a targeted site. The distribution characteristics of the compounds of formulas I and II may be assayed by following the protocols set forth in, for example, A. Leo et al., "Partition Coefficients and Their Uses", *Chemical Reviews*, 71, p. 535 (1971) and C. Hansch, "Linear Relationships Between Lipophilic Activity and Biological Activity of Drugs", *J. Pharm. Sci.*, 61, p.1 (1972).

The term "halogen" refers to fluorine, chlorine, bromine or iodine.

The term "heterocyclyl" refers to a stable 5–7 membered monocycle, 8–11 membered bicyclic heterocycle radical or an 8–16 membered tricyclic heterocycle which is may be saturated, mono-unsaturated or polyunsaturated, and which may be optionally benzofused if monocyclic. This term refers to both aromatic and non-aromatic heterocycles. Each heterocycle consists of carbon atoms and from one to four heteroatoms selected from the group consisting of nitrogen, oxygen and sulfur. As used herein, the terms "nitrogen and sulfur heteroatoms" include nitrogen and sulfur in any of their oxidation states, and the quaternized form of any basic nitrogen. The heterocyclyl radical may be attached through any atom of the cycle which results in the creation of a stable structure. Preferred heterocyclyl groups include, for example, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, tetrazolyl, thiazolidinyl, benzofianoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazoyl, benzodioxolyl, thiophenyl, tetrahydrothiophenyl and sulfolanyl.

The term "intrinsic activity or efficacy" refers to activity of a molecule with respect to alleviating the symptoms of immunoregulatory disorders, neuromuscular disorders, joint disorders, connective tissue disorders, circulatory disorders and pain. Intrinsic activity or efficacy may be associated with the interaction of that molecule with its targeted receptor. Intrinsic activity or efficacy of the compounds of formulas I and II may be assayed by following the procedure set forth in, for example, A. J. Clark, *J. Physiol.*, 61, p. 547 (1926); J. H. Gaddum, *J. Physiol.*, 61, p. 141 (1926); J. H. Gaddum, *J. Physiol.*, 89, p. 7p (1937); E. J. Ariens and A. M. Simonis, *J. Pharm. Pharmacol.*, 16, p. 289 (1964); or R. P. Stevenson, *Br. J. Pharmacol.*, 11, p. 379 (1956). Particularly relevant are the in vivo rat procedures outlined in the *CRC Handbook of Animal Models for the Rheumatic Diseases*, R. A. Greenwald and H. S. Diamond, eds., CRC Press (Boca Raton, Fla.) (1988)

The term "optionally substituted" refers to the substitution, if at all, of one or more hydrogen atoms in the unsubstituted moiety which results in the formation of a stable compound. Preferably, the moiety is substituted, if at all, at one to three positions. More preferably, the moiety is substituted, if at all, at only one position.

The term "pharmaceutically effective amount" refers to an amount effective to alleviate the symptoms of immunoregulatory disorders, neuromuscular disorders, joint disorders, connective tissue disorders, circulatory disorders and pain in a mammal, including a human.

The term "pharmaceutically acceptable carrier or adjuvant" refers to a carrier or adjuvant that may be administered to a mammal, including a human, together with a compound, mixture, or composition of this invention which is non-toxic and does not destroy the pharmacological activity of the compound, mixture or composition of this invention.

The term "ring system" refers to the radical of the corresponding cyclic moiety to which a given substituent is attached. For example, the ring system for compounds of formulas I and II is that portion of those compounds to which the substituents $R^1$, A and B are attached. The "aromatic ring system of any conventional anti-inflammatory or analgesic agent" refers to that portion of a known anti-inflammatory or analgesic compound that contains an aromatic ring system and which, when linked to the benzoylecgonine, ecgonine or ecgonidine portion of the compounds of this invention, results in the formation of a stable covalently coupled molecule. Preferred conventional anti-inflammatory and analgesic agents for use in the covalently coupled derivatives of this invention include, but are not limited to alkyl and aryl esters, salts and amides of salicylic acid (such as sodium salicylate, sodium thiosalicylate, magnesium salicylate, choline salicylate, carbethyl salicylate, phenol salicylate, salicylamide, aspirin (acetylsalicylic acid), aluminum aspirin, calcium acetylsalicylate, salsalate and flufenisal), N-arylanthranilic acids (such as mefenamic acid and meclofenamate sodium), arylacetic acid derivatives (such as indomethacin, sulindac, tolmetin, zomepirac, ibuprofen, naproxen, fenoprofen and piroxicam). More preferred conventional anti-inflammatory and analgesic agents for use in the covalently coupled derivatives of this invention are aspirin, naproxen and ibuprofen. We prefer coupling these conventional anti-inflammatory and analgesic agents to the free acid form of benzoylecgonine or ecgonine.

The covalently coupled benzoylecgonine, ecgonine and ecgonidine derivatives of this invention are represented by formulas I and II, respectively:

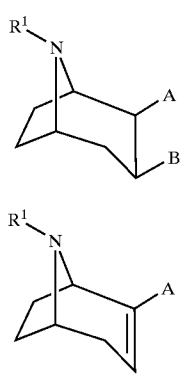

wherein:
  each $R^1$ is independently selected from the group consisting of H; $COR^2$; COBn; alkyl; alkenyl; and alkynyl, said alkyl, alkenyl and alkynyl being optionally substituted with OH, SH, $NH_2$, CN, $CF_3$ or halogen;
  A is —L—$(M)_p$;
  B is —L—$(M')_{p'}$;
  each p and p' is independently selected from the group consisting of 1 or 2;

each L is independently a linker which,
    (a) if linking one M or M' to the ring system, is selected from the group consisting of —$(CR^2R^2)_n$—CO—Q—; —$(CR^2R^2)_n$—Q—CO—; —$(CR^2R^2)_n$—O—C(OH)—; and —$(CR^2R^2)_n$—Q—; or
    (b) if linking two M or M', the same or different, to the ring system is

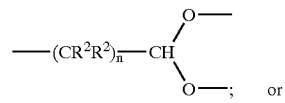

(c) if linking two ring. systems chosen from compounds of formulas I and II, the same or different, to M or M' is

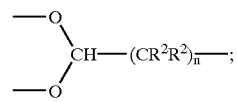

each n is independently selected from the group consisting of 0, 1, 2 and 3;
  each Q is independently selected from the group consisting of —NH—, —O— and —S—;
  each M and M' is independently a moiety that, either alone or in combination with other M or M' moieties, enhance the distribution characteristics, intrinsic activity or efficacy of said compound, provided that M is not a moiety having the formula —$CH_2$—CHX—$R^3$ when B is —O—CO—M', —O—M' or when B is not present (i.e., in compounds of formula II);
  each $R^2$ is independently selected from the group consisting of H; alkyl; alkenyl; alkynyl; alkoxy; aminoalkyl; haloalkyl; aryl; heterocyclyl; aralkyl; cycloalkyl; cycloalkylalkyl; halogen; aroyl; acyl; and aralkyl; any of said $R^2$ being optionally substituted with OH, SH, $NH_2$, oxo and halogen;
  X is selected from the group consisting of OH; SH; $NH_2$; and halogen; and
  $R^3$ is selected from the group consisting of alkyl, alkenyl and allcynyl, optionally substituted with OH, SH, $NH_2$ or halogen; $COCH_3$; COPh; and COBn.

Preferred compounds of formulas I and II are those wherein Q is —O—; M' is selected from the group consisting of —OH, O—$(CH_2)_n$-aryl and O—C(O)-aryl; and n is selected from the group consisting of 0 and 1.

Other preferred compounds of formulas I and II are those wherein A or B or both are independently selected from the group consisting of —$(CR^2R^2)_n$—O—CO—$(CR^2R^2)_n$—E, —$(CR^2R^2)_n$—CO—O—$CR^2R^2)_n$—E, —$(CR^2R^2)_n$—O—CH(OH)—$(CR^2R^2)_n$—E and —$(CR^2R^2)_n$—O—$CR^2R^2)_n$—E, wherein:
  each $R^2$ is independently selected from the group consisting of H; alkyl; alkenyl; alkynyl; alkoxy; aminoalkyl; haloalkyl; aryl; heterocyclyl; aralkyl; cycloalkyl; cycloalkylalkyl; halogen; aroyl; acyl; and aralkyl; any of said $R^2$ being optionally substituted with OH, SH, $NH_2$, oxo and halogen,
  each n is independently selected from the group consisting of 0, 1, 2 and 3; and
  E is the aromatic ring system of any conventional anti-inflammatory or analgesic agent.

More preferred compounds of formulas I and II are those wherein A or B or both are independently selected from the group consisting of —(CR²R²)ₙ—O—CO—(CR²R²)ₙ—E, —(CR²R²)ₙ—CO—O—(CR²R²)ₙ—E, —(CR²R²)ₙ—O—CH(OH)—(CR²R²)ₙ—E and —(CR²R²)ₙ—O—(CR²R²)ₙ—E, wherein:

each $R^2$ is independently selected from the group consisting of H; alkyl; alkenyl; alkynyl; alkoxy; aminoalkyl; haloalkyl; aryl; heterocyclyl; aralkyl; cycloalkyl; cycloalkylalkyl; halogen; aroyl, acyl; and aralkyl; any of said $R^2$ being optionally substituted with OH, SH, $NH_2$, oxo and halogen, each n is independently selected from the group consisting of 0, 1, 2 and 3; and E is selected from the group consisting of formulas III–VI:

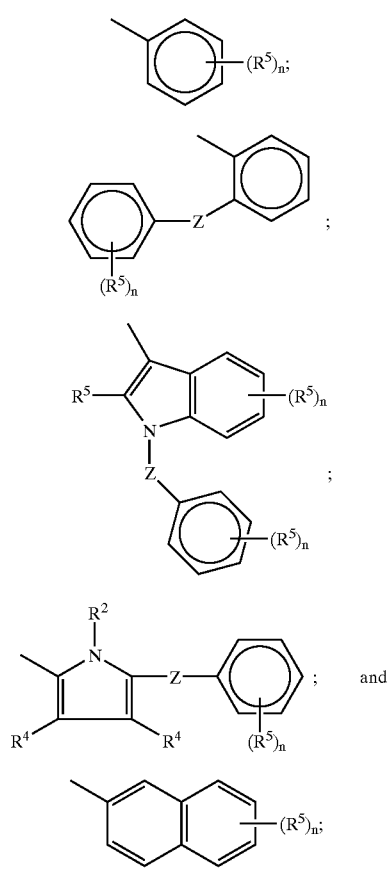

wherein:

each $R^4$ is independently selected from the group consisting of H, alkyl; alkenyl; alkynyl; acyl; aroyl; and halogen, said alkyl, alkenyl, alkynyl and carboalkyl being optionally substituted with OH, SH, $NH_2$, oxo and halogen; and each $R^5$ is independently selected from the group consisting of alkyl; alkenyl; alkynyl; alkoxy; aminoalkyl; haloalkyl; aryl; heterocyclyl; aralkyl; cycloalkyl; cycloalkylalkyl; halogen; aroyl, acyl; and aralkyl; any of said $R^5$ being optionally substituted with OH, SH, $NH_2$, oxo and halogen.

In each of the more preferred compounds of formulas I and II (i.e., wherein E is selected from the group consisting of formulas III–VII), we particularly prefer those compounds wherein A is selected from the group consisting of —$CH_2$—O—C(O)—E and —C(O)—O—$CH_2$—E and B is O—CO—Ph.

Most preferred compounds of formulas I and II are those having the structures of formulas VIII–XV:

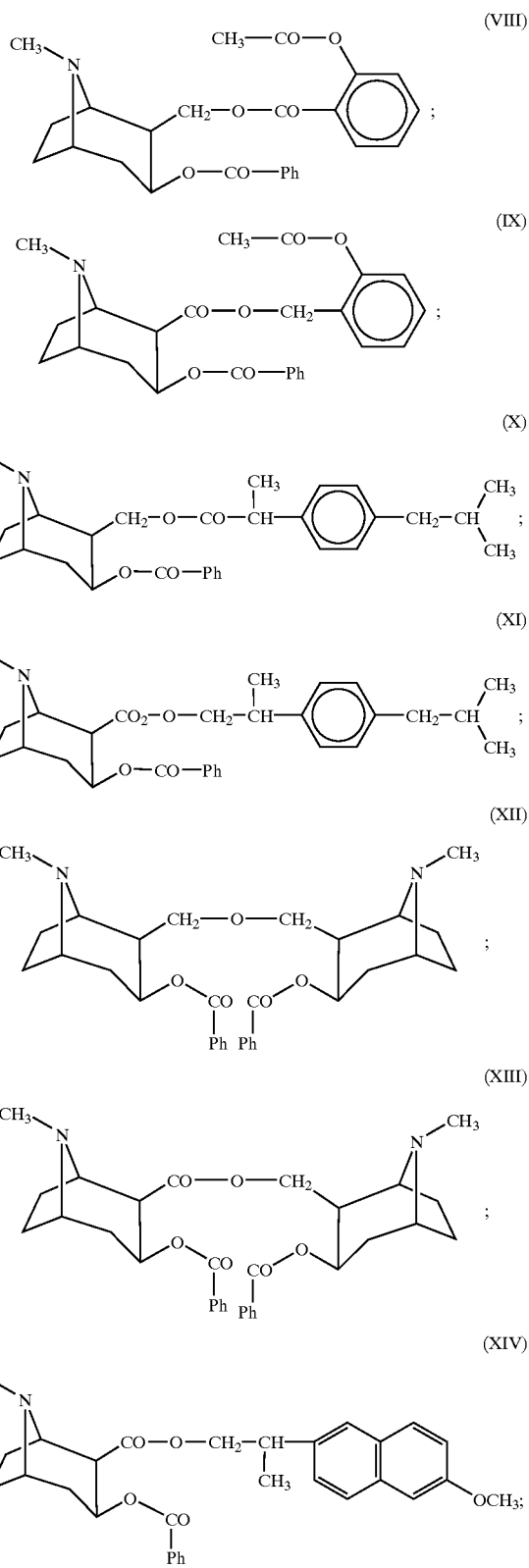

-continued (XV)

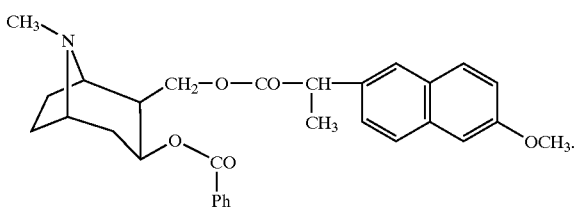

The compounds of formulas VIII and IX are covalently coupled benzoylecgonine-aspirin derivatives. The compounds of formulas X and XI are covalently coupled benzoylecgonine-ibuprofen derivatives. The compounds of formulas XII and XIII are covalently coupled benzoylecgonine-benzoylecgonine derivatives. The compounds of formulas XIV and XV are covalently coupled benzoylecgonine-naproxen derivatives.

The compounds of formulas I and II (including the preferred, more preferred and most preferred compounds listed above) are useful for alleviating the symptoms of immunoregulatory disorders, neuromuscular disorders, joint disorders, connective tissue disorders, circulatory disorders and pain. As the skilled artisan will appreciate, mixtures of two or more compounds of formulas I and II will also be usefull in any application where a single compound of formula I and II is useful.

While not wishing to be bound by theory, we believe that the compounds of this invention may act as prodrugs. We believe that under physiological conditions, hydrolysis or other metabolic processes (such as oxidation or O-dealkylation) slowly occur at the 2-β position of compounds of formulas I and II and possibly, at the 3-β position of compounds of formula I, resulting in the formation of the corresponding benzoylecgonine, ecgonine and ecgonidine compounds. Also, if, as in the cases of the preferred compounds of this invention, the metabolic by-product is also a therapeutically active compound, one or more additional therapeutically active compounds are formed along with the corresponding benzoylecgonine, ecgonine and ecgonidine compound. However, it should be noted that the compounds of this invention may also exhibit efficacy in their original, unhydrolyzed or unmetabilized form.

In their unhydrolyzed or unmetabilized form, compounds of formulas I and II are more readily absorbed into the bloodstream than the corresponding benzoylecgonine, ecgonine and ecgonidine compounds because of their increased lipophilicity. We believe that by derivatizing benzoylecgonine, ecgonine and ecgonidine at the 2- and 3-positions, the lipophilicity of these compounds is increased, while the desired properties of the corresponding benzoylecgonine, ecgonine and ecgonidine compounds are maintained or enhanced. By administering the compounds of this invention to a patient, greater amounts of the active ingredient will enter the bloodstream and reach the targeted area than if the benzoylecgonine, ecgonine and ecgonidine compounds themselves were administered at the same dosage level. Accordingly, the pharmaceutical effects of the benzoylecgonine, ecgonine and ecgonidine compounds will be enhanced at a lower dosage level without additional side effects.

In addition, when benzoylecgonine, ecgonine and ecgonidine are covalently coupled with other known anti-inflammatory or analgesic agents, those covalently coupled compounds will hydrolyze or otherwise be metabolized in the body to produce two or more active compounds. We believe that once hydrolysis or other metabolic processes have occurred, the active compounds will exert a substantial synergistic effect. This mechanism may also lead to better targeting of multiple therapeutic agents to a particular site (i.e., by delivering them together and by altering the lipophilicity, polarity and other pharmacochemical characteristics of the covalently coupled molecule). This mechanism may also be used as a prolonged action form, whereby the covalently coupled active compounds are slowly released in the body over a period of time. By delivering several active drugs in a single molecule, multiple drug delivery can be attained by single-dose therapy. This delivery system should result in a reduction of the side effects often associated with oral delivery of anti-inflammatory and analgesic agents. Importantly, gastrointestinal problems should be minimized because the majority of the hydrolytic and other metabolic processes that results in the formation of multiple active compounds occurs in the intestinal tract, not in the stomach.

The flexibility in the number and nature of the active components covalently linked in a single molecule is a unique feature of this invention. As described in formulas I and II above, one or two M or M' groups may be linked to the A and B positions in those molecules. Accordingly, one to four units of M or M' may be released as a result of hydrolysis. It should be noted that every one of the possible linkage points need not be hydrolyzable. For example, in a compound of formula I, position A may be occupied by a hydrolyzable moiety (such as —O—CO—$(CR^2R^2)_n$—E, wherein $R^2$, n and E are defined as above for compounds of formula I and II) while position B may be occupied by a non-hydrolyzable moiety (such as OH). In addition, two or more benzoylecgonine, ecgonine and ecgonidine molecules may be linked together (for example, see formulas XII and XIII above).

Furthermore, pharmacological effects which were previously unattainable using particular modes of administration (such as topical administration) can now be realized, due to the decrease in the required dosage level. And because of their increased solubility in solution, the actual administered amount of a pharmaceutical composition containing the compounds of this invention will be decreased, making the composition more easily applied and the treatment regimen more acceptable to the patient. Consequently, it is possible to administer effectively the compounds of this invention in a wide variety of dosage forms.

In addition, the compounds of formulas I and II in their unhydrolyzed or unmetabolized form are able to enter the central nervous system ("CNS") in an amount effective to treat certain CNS disorders (such as, for example, Parkinson's disease), without causing adverse side effects commonly associated with conventional centrally-active drugs (e.g., euphoria, tachycardia and vasoconstriction). We believe that in the prodrug form, the compounds of formulas I and II can penetrate the blood/brain barrier and then be hydrolyzed to the corresponding benzoylecgonine, ecgonine and ecgonidine compound (which could not have passed through the blood/brain barrier). In this manner, pharmaceutically effective amounts of benzoylecgonine, ecgonine and ecgonidine compounds can be successfully targeted to the CNS.

We also believe that the compounds of formulas I and II in their native, unhydrolyzed or unmetabolized form may be useful in alleviating the symptoms of the aforementioned disorders without subsequent formation of the benzoylecgonine, ecgonine and ecgonidine compounds via hydrolysis or other metabolic processes. Compounds of formulas I and II may, for example, act peripherally to improve circulation to the afflicted areas. In addition, by increasing the levels of peripherally circulating dopamine (for example, by preventing dopamine re-uptake at the synaptosome), the compounds of this invention may create a chemical sympathectomy.

Although the precise mode of action of the compounds of this invention is not known, one theory is that the compounds of formulas I and II undergo a chelation reaction with the fibers of the muscles and joint capsules, allowing the fibers of the connective tissue to relax and become elongated. This elongation of the connective tissue fibers would result in decreased inflammation by increasing circulation and muscle activity and by improving joint motion. This theory explains the positive therapeutic results experienced by patients having joint, neuromuscular, connective tissue and circulatory disorders.

Alternatively, the compounds of formulas I and II may act as chelating agents of certain neurotransmitters or co-factors in the body (such as, for example, calcium, sodium and potassium ions). The blood level of free neurotransmitters and co-factors has a direct effect on the functioning of ionic channels and consequently, on intracellular response to various stimuli (such as, for example, intracellular mediation of catecholamine response through the cAMP system). Therefore, the formation of chelation complexes may play a significant role in the pharmacological activity of the compounds of this invention. Under these chelation theories, the substitution of a highly polar or hydrogen bonding moiety in one or more L, L', M and M' located in positions A and B (such as a hydroxyl, thiol, amino or halogen substitutions) is particularly preferred.

Another alternative theory involves the intracellular degradation of the compounds of this invention, resulting in the production of certain analgesic, anti-oxidant and anti-inflammatory compounds (such as benzoic acid and salicylic acid). The in vivo production of such pharmaceutically active compounds would procure the benefit of those agents while avoiding many of the side effects associated with their administration (such as gastrointestinal and renal toxicity). The in vivo production of anti-oxidants might explain the impressive immunoregulatory effects shown by the compounds of this invention. Likewise, the production of analgesics and anti-inflammatory agents in the body would also help to explain the mode of action of the compounds of this invention in alleviating pain.

Another possible mode of action involves a reduction in prostaglandin synthesis by inhibiting the action of phospholipase. During conditions of inflammation, pain, fever and platelet aggregation, arachidonic acid is liberated from phospholipid fractions of cell membranes by phospholipase A2. The arachidonic acid is then converted to other products, such as intermediate cyclic endoperoxide prostaglandins. These intermediates produce pain, inflammation and vasoconstriction. Prostaglandins have many other biological actions, including the ability to produce erythema, edema, pain, fever, vasodilation and uterine contractions. Therefore, by inhibiting the synthesis of prostaglandins, many desired physical effects can be realized.

Other possible modes of action include inhibition of chemotaxis of cells implicated in the inflammatory process, inhibition of lysosomal membrane labilization, antagonistic effects on mediators other than prostaglandins (e.g., histamines and bradykinin), inhibition of the biosynthesis of mucopolysaccharides, uncoupling of oxidative phosphorylation, fibrinolytic activity and sulfhydryl-disulfide stabilization.

The compounds of this invention may be easily synthesized using known techniques. Compounds of formulas I and II having L or L' as a reversed ester linkage (i.e., —C(O)—O—) may be prepared from ecgonine or benzoylecgonine compounds by simple esterification of the free acid with the alcohol form of any desired M or M moiety. Compounds of formulas I and II having L or L' as acetal or hemiacetal linkers can also be prepared using known techniques. Typically, the free acid form of benzoylecgonine, ecgonine or ecgonidine compounds may be reduced to the corresponding alcohol. One mole of alcohol may then be reacted with one mole of the aldehyde or ketone form of the desired M or M' moiety to form a hemiacetal. Alternatively, two moles of alcohol may be reacted with one mole of the aldehyde or ketone form of the desired M or M' moiety to form an acetal. Similarly, the desired M or M' moiety may be converted to a corresponding alcohol, then reacted with the free acid form of benzoylecgonine, ecgonine or ecgonidine compounds to yield hemiacetals or acetals.

Compounds of formulas I and II having L or L' as ester linkages (i.e., (—O—C(O)—) may be readily prepared from the reduction of the free acid form of benzoylecgonine, ecgonine and ecgonidine compounds to the alcohol, followed by esterification of the free acid form of the desired M or M' moiety. Many of these techniques are described in A. H. Lewin et al., "2β-Substituted Analogues of Cocaine. Synthesis and Binding to the Cocaine Receptor", *J. Med. Chem.*, 35, pp. 135–40 (1992). It is well within the skill of the art to devise and carry out such reaction schemes.

As can be appreciated by a chemist of ordinary skill in the art, the simple synthetic schemes described above can be modified to produce any of the compounds of formulas I and II. Such modifications might involve alterations in the starting materials or the addition of further synthetic steps (such as functional group transformations). Depending on precisely how the synthetic scheme is modified, the specific reaction conditions (such as the precise temperature and reaction times) might also require modification. Since the progress of these reactions can be easily monitored by techniques such as high performance liquid chromatography, gas chromatography, mass spectroscopy, thin layer chromatography, nuclear magnetic resonance spectroscopy and the like, such modifications are well within the skill of the art.

The compounds of this invention, and mixtures thereof, may be administered alone or in combination with other compounds, such as, for example, benzoylecgonine, ecgonine and ecgonidine compounds. When a compound of formula I or II, or a mixture thereof, is administered together with benzoylecgonine, ecgonine or ecgonidine, the therapeutic efficacy of the latter compounds may be enhanced. We prefer that pharmaceutical compositions comprising a compound of this invention, or a mixture thereof, in combination with benzoylecgonine, ecgonine and/or ecgonidine contain at least 5%, but more preferably at least 10%, of the compound or compounds of formulas I and II (w/w). We also prefer pharmaceutical compositions of this invention, and the mixtures contained therein, wherein no more than 0.1% cocaine (w/w) is present.

This invention also envisions the administration of the compounds of formulas I and II in combination with conventional therapeutic agents. Advantageously, such combination therapies utilize lower dosages of those conventional therapeutics, thus avoiding possible toxicity and adverse side effects incurred when those agents are used as monotherapies. For example, the compounds of this invention may be used in combination with conventional cancer drugs (such as, for example, methotrexate, taxol, 5-fluorouracil, cis-platinum, cortisone, nitrogen mustards, thiotepa and nitrosoureas), arthritis drugs (such as, for example, nonsteroidal anti-inflammatory agents, penicillamine, methotrexate, cortisone and gold salts) and neurological agents (such as, for example, amantadine, L-DOPA and CNS-anticholinergics).

According to this invention, the compounds of formulas I and II, or mixtures thereof, and the pharmaceutical compositions containing those compounds, may be administered to any mammal, including a human. The compounds and pharmaceutical compositions of this invention may be administered in any pharmaceutically acceptable dosage form, including, but not limited to intravenously, intramuscularly, subcutaneously, intra-articularly, intrasynovially, intrathecally, periostally, intratumorally, peritumorally, intralesionally, perilesionally, by infusion, sublingually, buccally, transdermally, orally, topically or by inhalation. We prefer oral, topical and transdermal administration and administration by inhalation.

Dosage forms may include pharmaceutically acceptable carriers and adjuvants which are known to those of skill in the art. These carriers and adjuvants include, for example, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Adjuvants for topical or gel base forms of the compounds and compositions of this invention include, but are not limited to, sodium carboxymethylcellulose, polyacrylates, waxes, polyoxyethylene-polyoxypropylene-block polymers, polyethylene glycol, propylene glycol and wool fat. For topical applications, we prefer to use propylene glycol.

For all administrations, conventionally administered dosage forms may be used. Such forms include, for example, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th edition, Lea and Febiger 1990).

The compounds and pharmaceutical compositions of this invention may be employed in a conventional manner to alleviate the symptoms of any of the aforementioned disorders (i.e., by administration to a mammal, including a human, a pharmaceutically effective amount of a pharmaceutical composition of this invention). Such methods and their dosage levels and requirements are well-recognized in the art and may be chosen by those of ordinary skill in the art from the available methods and techniques. Typically, dosage levels range from about 25–200 mg/dose for a 70 kg patient. Although one dose per day is often sufficient, up to 5 doses/day may be given. For oral doses, up to 1500 mg/day may be required. A typical treatment regimen for a 70 kg patient with a joint disorder (such as rheumatoid arthritis) or an immunoregulatory disorder (such as an autoimmune disease) is four doses/day (200 mg/dose), topically applied for two weeks. However, some disorders (such as osteoarthritis) require only 1 dose/day for two days. Once the symptoms of the disorder have receded, maintenance doses can be administered on a p.r.n. basis. As the skilled artisan will appreciate, lower or higher doses than those recited above may be required. Specific dosage and treatment regimens will depend on such factors as the patient's general health status, the severity and course of the patient's disorder or disposition thereto and the judgment of the treating physician.

Immunoregulatory disorders that may be treated with the compounds and compositions of this invention include, but are not limited to: inflammation, autoimmune diseases, allergies (such as, for example, insect bites and stings (e.g., mosquito, fire ant, bee or fly), poison ivy, poison oak and contact dermatitis.

Neuromuscular disorders that may be treated with the compounds and compositions of this invention include, but are not limited to: amyotrophic lateral sclerosis, multiple sclerosis, skeletal muscle trauma, spasm post-stroke, loss of sensory acuity, weakness, cerebral edema, Reiter's syndrome, polymyositis, Parkinson's disease, Huntington's disease, angina and acute back strain.

Joint disorders that may be treated with the compounds and compositions of this invention include, but are not limited to: frozen shoulder, restricted range of motion, post-fracture contracture, arthritis (such as, for example, rheumatoid arthritis, osteoarthritis, mixed arthritis, psoriatic arthritis, gout, inflammatory gout or juvenile rheumatoid arthritis), bursitis, ankylosing spondylitis, rheumatoid vasculitis and joint rigidity.

Connective tissue disorders that may be treated with the compounds and compositions of this invention include, but are not limited to: systemic lupus, Burger's disease, periarteritis nodosum, proliferative diseases (e.g., keloid scar formation, excessive scar formations, sanctity of scarified fibers and proliferative cancers such as carcinomas and sarcomas), scleroderma and collagen disorders.

Circulatory disorders that may be treated with the compounds and compositions of this invention include, but are not limited to: angina pectoris, myocardial ischemia, gangrene and diabetes (such as diabetes mellitus and diabetes insipidus).

We believe that the compounds and compositions of this invention are especially well suited for use in alleviating pain and alleviating the symptoms of inflammation, Parkinson's disease, acute back strain, restricted range of motion, arthritis, bursitis, ankylosing spondylitis, Burger's disease and myocardial ischemia.

In order that this invention be more fully understood, the following examples are set forth. These examples are for the purpose of illustration only, and are not to be construed as limiting the scope of the invention in any way.

CHEMICAL SYNTHESES

In the following examples, these instruments and procedures are used:

GC/MS analyses are performed on a Finnigan Model 9610 gas chromatograph4000 Mass Spectrometer equipped with an IBM-AT computer using Teknivent Vector/one data system software (St. Louis, Mo.). The mass spectrometer is calibrated using perfluorotributylamine. Chromatographic separations are achieved on a 30 mm×0.32 mm, 0.25 $\mu$m film thickness dimethysilicone fused silica capillary column (BD-1, J&W Scientific, Folson, Calif.). Ultra pure helium is used as the carrier gas and compressed air is used as the make up gas (Sunox Inc., Charleston, S.C.).

Reagents and samples are weighed on a microbalance type 2406 (range 0–20 g, Sartorius Werke GMBH Gottigen, Germany), microbalance type 4503 (range 0–1 g, Sartorius Werke GMBH (Gottingen, Germany), or a microbalance type 2842 (range 0–160 g, Sartorius Werke GMBH Gottigen, Germany).

A Vortex-Genie (Scientific Industries, Inc. Bohemia, N.Y.) is used to mix standards. A Varian Aerograph series 1400 gas chromatographic oven is used to heat all samples requiring derivatization. A Fisher Isotem 500 series drying oven is used for drying glassware.

Three necked round bottomed flasks (250 ml, 50 ml, 100 ml and 500 ml) are used for synthesis. Centrifuge tubes (15 ml) are silanized with a solution of dimethyldichlorosilane in toluene. Disposable borosilicate pipettes (1, 5, and 10 ml) by Fisher Scientific Company are used. Derivatizing reactions are carried out using teflon lined 1, 2, and 3 dram vials. All other glassware is routine scientific glassware for synthetic or analytical purposes. The HPLC analyses are performed with an HPLC system which consisted of a Beckman M45 delivery pump, Model Lambda Max 481 LC spectrophotometer variable wavelength UV absorbance detector equipped with an automatic sampling Wisp injector model 710B accessory and a Shimadzu C-R3A Chromatopac integrator. The stationary phase is a reversed phase C18 column ($\mu$m Bondapak of Millipore, P/N 27324, (3.9 mm ID×30 cm).

Thin layer chromatography (TLC) is performed on Whatman silica gel 60 TLC plates.

All HPLC analyses are performed with the UV detector operating at 232 wavelength. The mobile phase is 20% v/v acetonitrile in 0.01 M $KHPO_4$ (pH range 2.1–2.9) with a flow rate of 2.0 ml/min. The injection volume is 15 $\mu$l and operating range as 0.1 AUFS. No internal standard is utilized for HPLC.

A filter holder (Fisher brand) assembly with a 300 ml fritglass support (47 mm) is used to degas the HPLC mobile phase. Filter papers (0.22 $\mu$, Lazar Scientific, Los Angeles, Calif.) are used to filter the mobile phase for the HPLC assay.

Homatropine hydrobromide, pentafluoro-propionic anhydride (PFPA), and pentafluoropropanol (PFP) are obtained from Aldrich Chemical Co. (Milwaukee, Wis.).

A high line vacuum is used to evaporate or distill propylene glycol solution.

Solvents from derivatization are removed by evaporating (with evaporating needles) under a stream of nitrogen. Solvents requiring heat during evaporation are heated in a sand bath.

All mass spectrometric analyses utilize the Finnigan system. The helium gas linear velocity is at 50 cm/s. The data system scan rate is every 0.2 s with a sweep width of 0.1 $\mu$, integrating each acquisition sample for 4 ms. Perfluorotributylamine is used to calibrate the MS. Electron impact ionizing voltage is at 60 eV and ionizing current at 300 $\mu$A. The electron multiplier is operated at 1700 V. With injection port and MX ion source temperature set at 250° C. and 260° C., respectively, separation is achieved using a multi-linear programmed temperature initially at 130° C. and increased to 140° C. at 2°/min, then finally to 258° C. at 17 °/min. When isothermal conditions are used, the column temperature is maintained at 160° C., 185° C., 200° C., or 220° C. For a typical analytical procedure, 0.05 $\mu$l or 0.1 $\mu$l with an equal amount of air is quickly injected into the GC injection port. Upon injection of the sample, temperature programming begins, acquisition is monitored, and the filament is activated 1.5 min after injection of sample.

Derivatization of the compounds is performed before GC/MS analysis. 10 $\mu$l of the compound to be derivatized is placed in a teflon capped vial and derivatized with the 35 $\mu$l volume of PFP and 70 $\mu$l PFPA. The vial is heated at 100° C. for 20 min, cooled, excess reagents evaporated, reconstituted with acetonitrile to the desired volume, and then analyzed on GC/MS.

Cocaine base is prepared by the following protocol: Cocaine HCl (5.0 g) is dissolved in 150 ml of distilled water. Volumes of 1 N KOH are added with stirring to a final pH of about 10. The white solid formed is padded dry using filter paper and paper towel. The solid is then placed in a 500 ml beaker and allowed to melt in a 100° C. to 110° C. oil bath. Once the solid is completely melted, the beaker is removed and allowed to cool to room temperature. The excess water is decanted and the crystallized cocaine base allowed to air dry.

Benzoylecgonine is synthesized by the following protocol: Cocaine base (9.3 g) is mixed with 200 ml of distilled water and allowed to reflux for 5 hr. The resultant solution is cooled and extracted five times with diethyl ether. The aqueous layer is evaporated under reduced pressure and the residue is recrystallized from water. Needle shaped white crystals are collected (approximate yield: 50%).

Ecgonine HCl is synthesized by direct acid hydrolysis of cocaine using the protocol described in M. R. Bell and S. Archer, "L(+)-2-Tropinone", *J. Amer. Chem. Soc.*, 82, pp. 4642–44 (1960): Cocaine HCl (9.0 g) is dissolved in 10 ml of 12 N HCl and 150 ml of distilled water and refluxed for 15 hr. The resultant solution is cooled and extracted five times with diethyl ether, the aqueous phase is combined and evaporated under reduced pressure. The residue is recrystallized from ethanol and water to yield white crystals (approximate yield: 50%).

Structure elucidation is performed by GC/MS and confirmed by the observed retention times of the fluorinated derivatives and the observed MS fingerprint fragment ions.

Benzoylecgonine is reduced to the corresponding alcohol (i.e., 3 β-(benzoyloxy)-2β-(hydroxymethyl)-8-methyl-8-azabicyclo[3.2.1]octane) using the following protocol:

To a stirred suspension of benzoylecgonine (1.45 g, 5 mmol) in freshly distilled TBF (75 ml) at 0° C. is added dropwise diborane-THF complex (18 ml, 18 mmol) over a period of 15 minutes. After stirring at 0° C. for another 2 hour and then at room temperature for 1 hour, excess diborane is carefully destroyed by the addition of MeOH. The mixture is acidified to pH 1 with 6N HCL and concentrated by evaporation. The solution is then basified with 6N $NH_4OH$ and extracted with $CH_2Cl_2$. The concentrated extract is dried (over $Na_2SO_4$) and evaporated. The residue is purified by thin-layer chromatography eluting with 10% MeOH/$CH_2Cl_2$. The fractions containing the product are pooled, evaporated and crystallized from $CH_2Cl_2$/petroleum ether (approximate yield 30%). In the examples that follow, this product is referred to as BEc(OH).

EXAMPLE 1

Synthesis of Compound VIII

To a stirred solution of BEc(OH) (155 mg, 0.55 mmol) and $Et_3N$ (0.2 ml, 1.4 mmol) in $CH_2Cl_2$ (5 ml) at room temperature is added dropwise a solution of 2-[acetoxy]-benzoic acid chloride (1.2 mmol) in $CH_2Cl_2$. After 3 hours, the mixture is treated with $H_2O$ (2 ml). The organic phase is separated and the aqueous phase is extracted with $CH_2Cl_2$ (2×5 ml). The combined organic extract is washed with $H_2O$ and dried over $Na_2SO_4$. Removal of the solvent yields compound VIII.

EXAMPLE 2

Synthesis of Compound X

To a stirred solution of BEc(OH) (155 mg, 0.55 mmol) and $Et_3N$ (0.2 ml, 1.4 mmol) in $CH_2Cl_2$ (5 ml) at room temperature is added dropwise a solution of 2-methyl-2-[para-isobutylphenyl]-acetic acid chloride (1.2 mmol) in CH$_2$Cl$_2$. After 3 hours, the mixture is treated with H$_2$O (2 ml). The organic phase is separated and the aqueous phase is extracted with CH$_2$Cl$_2$ (2×5 ml). The combined organic extract is washed with H$_2$O and dried over Na$_2$SO$_4$. Removal of the solvent yields compound X.

EXAMPLE 3

Synthesis of Compound XIII

To a stirred solution of BEc(OH) (155 mg, 0.55 mmol) and Et$_3$N (0.2 ml, 1.4 mmol) in CH$_2$Cl$_2$ (5 ml) at room temperature is added dropwise a solution of the acid chloride of benzoylecgonine (1.2 mmol) in CH$_2$Cl$_2$. After 3 hours, the mixture is treated with H$_2$O (2 ml). The organic phase is separated and the aqueous phase is extracted with CH$_2$Cl$_2$ (2×5 ml). The combined organic extract is washed with H$_2$O and dried over Na$_2$SO$_4$. Removal of the solvent yields compound XIII.

EXAMPLE 4

Synthesis of Compound XV

To a stirred solution of BEc(OH) (155 mg, 0.55 mmol) and Et$_3$N (0.2 ml, 1.4 mmol) in CH$_2$Cl$_2$ (5 ml) at room temperature is added dropwise a solution of 2-methyl-2-[6-methoxy-2-naphthyl]-acetic acid chloride (1.2 mmol) in CH$_2$Cl$_2$. After 3 hours, the mixture is treated with H$_2$O (2 ml). The organic phase is separated and the aqueous phase is extracted with CH$_2$Cl$_2$ (2×5 ml). The combined organic extract is washed with H$_2$O and dried over Na$_2$SO$_4$. Removal of the solvent yields compound XV.

While we have described a number of embodiments of this invention, it is apparent that our constructions may be altered to provide other embodiments which utilize the basic teachings of this invention. Therefore, it will be appreciated that the scope of this invention is to be defined by the appended claims, rather than by the specific embodiments which have been presented by way of example.

What is claimed is:

1. A composition comprising an effective amount of a compound having the structure of any one of formulas VIII–XV:

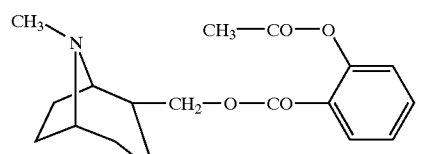
(VIII)

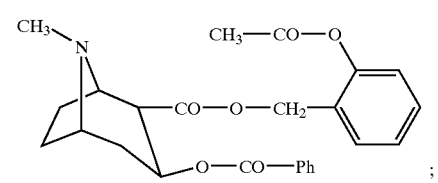
(IX)

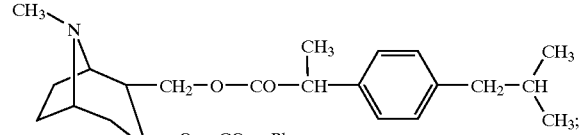
(X)

* An "Appendix to Amendments" is enclosed at Exhibit A, showing the amendments to the claims. In the Appendix, the added portion of text is underscored and the deleted portion is bracketed.

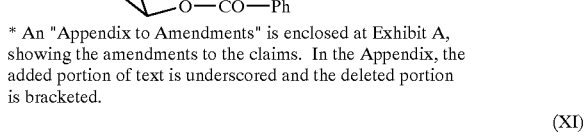
(XI)

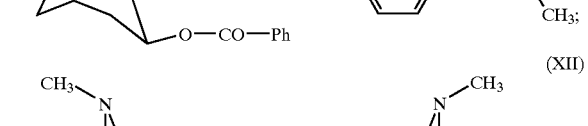
(XII)

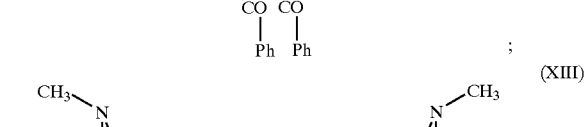
(XIII)

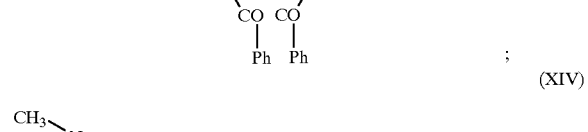
(XIV)

and

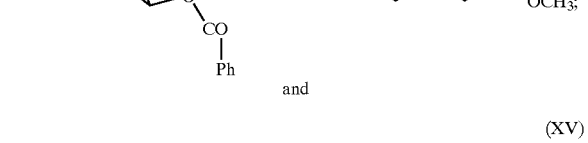
(XV)

or a mixture thereof;
in combination with an effective amount of aspirin or acetaminophen.

2. The composition according to claim 1, wherein the compound or mixture thereof is in the form of a pharmaceutically acceptable salt.

3. A pharmaceutical composition comprising the composition according to claim 1 or 2 and a pharmaceutically acceptable carrier or adjuvant.

4. A pharmaceutical composition comprising the composition according to claim 1 or 2 and a pharmaceutically acceptable carrier or adjuvant, wherein the composition comprises a mixture of at least two compounds according to claim 1 or 2.

5. The pharmaceutical composition according to claim 3 or 4, further comprising at least one additional ingredient selected from the group consisting of benzoylecgonine, ecgonine and ecgonidine.

6. The pharmaceutical composition according to claim 3, 4 or 5, wherein the composition comprises at least about 5% of a mixture of at least two compounds according to claim 1.

7. A pharmaceutical composition according to claim 3, 4, 5 or 6, wherein the composition is in an administering dosage form selected from the group consisting of a tablet, capsule, caplet, liquid, solution, suspension, emulsion, lozenges, syrup, reconstitutable powder, granule, suppository and transdermal patch.

8. A method for treating the symptoms of immunoregulatory disorders, neuromuscular disorders, joint disorders, connective tissue disorders, circulatory disorders or pain comprising the step of administering to a mammal, including a human, a pharmaceutically effective amount of the pharmaceutical composition according to claims 3–6.

9. The method according to claim 8, wherein the disorder is selected from the group consisting of pain, inflammation, autoimmune diseases, allergies, poison ivy, poison oak, contact dermatitis, multiple sclerosis, skeletal muscle trauma, spasm post-stroke, loss of sensory acuity, weakness, cerebral edema, Reiter's syndrome, polymyositis, Parkinson's disease, Huntington's disease, angina, acute back strain, frozen shoulder, restricted range of motion, post-fracture contracture, arthritis, bursitis, ankylosing spondylitis, rheumatoid vasculitis, joint rigidity, osteoarthritis, mixed arthritis, psoriatic arthritis, gout., inflammatory gout, juvenile rheumatoid arthritis, systemic lupus, Burger's disease, periarteritis nodosum, proliferative diseases, scleroderma, collagen disorders, angina pectoris, myocardial, ischemia.

10. The method according to claim 9 or 8, wherein the pharmaceutical composition is to be administered intravenously, intramuscularly, subcutaneously, intraarticularyl, intrasynovially, intrathecally, periostally, intratumorally, peritumorally, intralesionally, perilesionally, by infusion, sublingually, buccally, transdermally, orally, or topically.

* * * * *

UNITED STATES PATENT AND TRADEMARK OFFICE
CERTIFICATE OF CORRECTION

PATENT NO. : 6,482,831 B1 Page 1 of 2
DATED : November 19, 2002
INVENTOR(S) : Wynn et al.

It is certified that error appears in the above-identified patent and that said Letters Patent is hereby corrected as shown below:

<u>Title page, Item [54] and Column 1, line 2,</u>
Title, change "EGCONINE" to -- ECGONINE --;

<u>Title page,</u>
Item [60], Related U.S. Application Data, change "PCT/US95/09726" to
-- PCT/ US95/07268 --;

<u>Column 2,</u>
Line 16, change "(Kp;" to -- $(M)_p$; --;

<u>Column 3,</u>
Line 24, change "ans" to -- trans --;
Line 64, change "alcyl radical" to -- alkyl radical --;

<u>Column 4,</u>
Line 36, change "benzofianoyl" to -- benzofuranoyl --;

<u>Column 6,</u>
Line 43, change "allcynyl" to -- alkynyl --;
Line 52, change $2^{nd}$ occurrence of "$CR^2R^2)_n$" to -- $(CR^2R^2)_n$ --;
Line 54, change $3^{rd}$ occurrence of "$CR^2R^2)_n$" to -- $(CR^2R^2)_n$ --;

<u>Column 7,</u>
Line 13, change "III-VI" to -- II - VII --;

<u>Column 8</u>
Line 31, in formula (XI), change "$CO_2-O-CH_2-\underset{\underset{CH_3}{|}}{C}H$" to
-- $CO-O-CH_2-\underset{\underset{CH_3}{|}}{C}H$ --;

UNITED STATES PATENT AND TRADEMARK OFFICE
CERTIFICATE OF CORRECTION

PATENT NO.    : 6,482,831 B1
DATED         : November 19, 2002
INVENTOR(S)   : Wynn et al.

It is certified that error appears in the above-identified patent and that said Letters Patent is hereby corrected as shown below:

Column 12,
Line 6, change 2$^{nd}$ occurrence of "M" to -- M$'$ --;

Column 20,
Line 17, change "myocadial, ischemia" to -- myocardial ischemia --;
Line 21, change "intraarticularyl" to -- intraarticularly --.

Signed and Sealed this

First Day of June, 2004

JON W. DUDAS
*Acting Director of the United States Patent and Trademark Office*